United States Patent [19]
Andruszkiewicz et al.

[11] Patent Number: 5,863,937
[45] Date of Patent: Jan. 26, 1999

[54] PHARMACEUTICAL COMPOSITIONS

[75] Inventors: Ryszard Andruszkiewicz, Sopot; Henryk Chmara; Teresa Zieniawa, both of Gdansk; Edward Borowski, Gdansk, all of Poland

[73] Assignee: BTG International Limited, London, United Kingdom

[21] Appl. No.: 624,559

[22] PCT Filed: Oct. 5, 1994

[86] PCT No.: PCT/GB94/02162

§ 371 Date: Apr. 8, 1996

§ 102(e) Date: Apr. 8, 1996

[87] PCT Pub. No.: WO95/09867

PCT Pub. Date: Apr. 13, 1995

[30] Foreign Application Priority Data

Oct. 7, 1993 [PL] Poland ..................................... 300659

[51] Int. Cl.$^6$ ...................... A61K 31/335; A61K 38/00
[52] U.S. Cl. .............................. 514/449; 514/19; 549/512
[58] Field of Search ........................ 514/19, 449; 549/512

[56] References Cited

FOREIGN PATENT DOCUMENTS 0 353 317   2/1990   European Pat. Off. .
WO 93/12138   6/1993   WIPO .

OTHER PUBLICATIONS

R. Andruszkiewicz et al. "Anticandidal properties of N$^3$–(4–Methoxyfumaroyl). . ." J. Med. Chem. 1990, 33, pp. 132–135.
R. Andruszkiewicz et al. "Synthesis and biological properties of N$^3$–. . . ." J. Med. Chem., 1987, 30, pp. 1715–1719.
D.F. Rane et al. "Total synthesis and absolute. . . " Tetrahedron Letters, vol 34 No 30, pp. 3201–3204, 1993.
R. Andruszkiewicz et al. "Synthesis and Anticandiadal activites. . ." The Journal of Antibiotics, vol 17 No 6, pp. 715–723.
J. Shoji et al. "Isolation of CB–25–1, and antifungal. . ." The Journal of Antibiotics, vol XLII No 6, pp.869–873.
R. Cooper et al. "Sch 37137, a novel antifungal compound. . ." The Journal of Antibiotics, vol XLI No. 1, pp. 13–19.

*Primary Examiner*—Amelia Owens
*Attorney, Agent, or Firm*—Nixon & Vanderhye

[57] ABSTRACT

New derivatives of N$^3$-D-trans-2,3-epoxysuccinamoyl-L-2, 3-diaminopropanoic acid of formula (1)

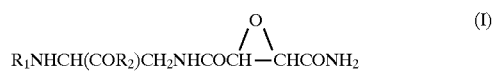

wherein R$_1$ is hydrogen;
or R$_1$ is the residue of an amino acid selected from L-valine, L-norvaline, L-leucine, L-isoleucine, L-norleucine, L-methionine, L-lysine, L-2-aminobutanoic acid, L-aspartic acid and L-glutamic acid;
or R$_1$ is the residue of a dipeptide selected from L-norvalyl-L-norvaline, L-lysyl-L-norvaline, L-methionyl-L-norvaline, L-glutamyl-L-norvaline, L-norvalyl-L-methionine, L-methionyl-L-methionine, L-leucyl-L-norvaline, L-norleucyl-L-norvaline, L-valyl-L-norvaline, L-glutamyl-L-leucine, L-asparginyl-L-norvaline and L-leucyl-L-leucine;
wherein R$_2$ is hydroxyl;
or R$_2$ is the residue of an amino acid selected from L-alanine, L-methionine, L-valine, L-norvaline, L-leucine, L-isoleucine, L-norleucine and L-2-aminobutanoic acid; with the provisos that when R$_1$ is hydrogen then R$_2$ is an amino acid residue and that when R$_1$ is an amino acid residue or a peptide residue then R$_2$ is hydroxyl; the derivative optionally being in the form of a physiologically acceptable salt thereof; are of value as antimicrobial agents, particularly as antifungal agents, especially in relation to *Candida albicans*.

20 Claims, No Drawings

PHARMACEUTICAL COMPOSITIONS

This invention relates to novel derivatives of $N^3$-D-trans-2,3-epoxysuccinamoyl-L-2,3-diaminopropanoic acid of value as antimicrobial agents.

Fungal infections, caused mainly by *Candida albicans*, have increased rapidly in the last decade, especially in immunocompromised patients such as those with AIDS, those receiving organ transplants and cancer patients undergoing chemotherapy. Such infections can lead to secondary infections that are life threatening. Amphotericin B is still the drug of choice for most fungal diseases and the more recently developed antifungal drugs do not in general offer any substantial improvement as compared with amphotericin B. There is still therefore a need for new antifungal drugs.

The compound $N^2$-L-alanyl-$N^3$-D-trans-2,3-epoxysuccinamoyl-L-2,3-diamino-propanoic acid, identified as Sch 37137, is produced by fermentation from *Micromonospora sp.* (Cooper et al., J. Antibiotics, 1988, 41, 13 and the absolute configuration of all the chiral centres in this compound has been established through a correlation of the product of fermentation with a synthetic compound (Rane et al., Tetrahedron Letters, 1993, 34(20), 3201). Sch 37137 displays biological activity against certain fungi and gram-positive and gram-negative bacteria although the activity reported by Cooper et al. was at only a relatively low level.

Nevertheless, we have now found that Sch 37137, and more particularly novel analogues of Sch 37137 in which the L-alanine residue is replaced by certain alternative amino acid residues or in which other variations in structure are made, possess good levels of antimicrobial activity, the activity of the analogues generally being enhanced as compared with that of the corresponding isomeric form of Sch 37137.

Accordingly, the present invention comprises a compound being a derivative of $N^3$-D-trans-2,3-epoxysuccinamoyl-L-2,3-diaminopropanoic acid of formula (1)

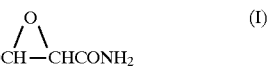

(I)

wherein $R_1$ is hydrogen;
    or $R_1$ is the residue of an amino acid selected from L-valine, L-norvaline, L-leucine, L-isoleucine, L-norleucine, L-methionine, L-lysine, L-2-aminobutanoic acid, L-aspartic acid and L-glutamic acid;
    or $R_1$ is the residue of a dipeptide selected from L-norvalyl-L-norvaline, L-lysyl-L-norvaline, L-methionyl-L-norvaline, L-glutamyl-L-norvaline, L-norvalyl-L-methionine, L-methionyl-L-methionine, L-leucyl-L-norvaline, L-norleucyl-L-norvaline, L-valyl-L-norvaline, L-glutamyl-L-leucine, L-asparginyl-L-norvaline and L-leucyl-L-leucine;
wherein $R_2$ is hydroxyl;
    or $R_2$ is the residue of an amino acid selected from L-alanine, L-methionine, L-valine, L-norvaline, L-leucine, L-isoleucine, L-norleucine and L-2-aminobutanoic acid; with the provisos that when $R_1$ is hydrogen then $R_2$ is an amino acid residue and that when $R_1$ is an amino acid residue or a peptide residue then $R_2$ is hydroxyl; the compound optionally being in the form of a physiologically acceptable salt.

It will be appreciated that the amino acid and dipeptide residues $R_1$ are formed at the C-terminus of the amino acid or dipeptide whilst the amino acid residues $R_2$ are formed at the N-terminus.

A preferred group of compounds of formula (1) has the formula (2)

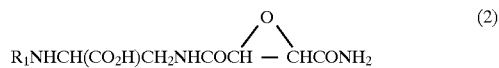

wherein $R_1$ is the residue of an amino acid selected from L-valine, L-norvaline, L-leucine, L-isoleucine, L-norleucine, L-methionine, L-lysine, L-2-aminobutanoic acid, L-aspartic acid and L-glutamic acid;
    or $R_1$ is the residue of a dipeptide selected from L-norvalyl-L-norvaline, L-lysyl-L-norvaline, L-methionyl-L-norvaline, L-glutamyl-L-norvaline, L-norvalyl-L-methionine, L-methionyl-L-methionine, L-leucyl-L-norvaline, L-norleucyl-L-norvaline, L-valyl-L-norvaline, L-glutamyl-L-leucine, L-asparginyl-L-norvaline and L-leucyl-L-leucine.

Preferred compounds of formula (2) in which $R_1$ is a dipeptide residue comprise a norvaline residue, as one of the residues of the dipeptide, particularly at its C-terminus. Thus a dipeptide residue $R_1$ of particular interest is that of L-lysyl-L-norvaline. However it is generally preferred that $R_1$ is an amino acid residue rather than a dipeptide residue, particularly the residue of L-methionine or L-leucine and especially that of L-norvaline.

A further preferred group of compounds of formula (1) has the formula (3)

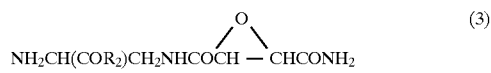

wherein $R_2$ is the residue of an amino acid selected from L-alanine, L-methionine. L-valine, L-norvaline, L-leucine, L-norleucine and L-2-aminobutanoic acid. Preferences for $R_2$ are as for the amino acid residues $R_1$ with an L-norvaline residue being of especial interest but in general a compound of formula (2) in which $R_1$ is an amino acid residue has higher antimicrobial activity than the corresponding compound of formula (3) in which $R_2$ is derived from the same amino acid.

It will be appreciated that the compounds (1) are of a specific configuration, as defined hereinbefore, at each of the chiral centres therein. However, the present invention does include such compounds when in admixture with compounds having a different configuration at one or more of these chiral centres. Thus the compounds may exist in the racemic form or, more particularly in the form of the diastereoisomeric mixture in which the other component of the mixture contains the L-trans (2 S, 3 S) form of the 2,3-epoxysuccinamoyl group rather than the D-trans (2 R, 3 R) form. However, in view of the enhanced activity of the compounds of the defined stereochemistry, the D-trans form generally being approximately 20 times as active as the L-trans form, it is preferred that the compounds are used in a form substantially free, i.e. containing 20% and particularly 10% or less by weight, of other isomers.

As indicated the compounds (1) may optionally be used in the form of a physiologically acceptable salt. These salts may be of two types, being formed with either physiologically acceptable bases or acids. Examples of suitable bases are the alkali metal hydroxides, for example sodium hydroxide, quaternary ammonium hydroxides and amines such as tris (tris representing 2-amino-2-hydroxymethyl propane 1,3-diol). Suitable acids may be inorganic or organic. Examples of such inorganic acids are phosphoric acid, nitric acid, sulphuric acid and the hydrohalic acids hydrochloric acid, hydrobromic acid and hydroiodic acid. Examples of such organic acids are citric acid, oxalic acid, fumaric acid, maleic acid, lactic acid, succinic acid, malic acid, tartaric acid, methane sulphonic acid and trifluoroacetic acid.

In general, the compounds (1) may be prepared via a compound of formula (4)

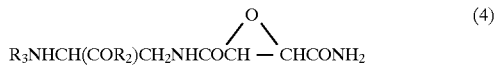

$$R_3NHCH(COR_2)CH_2NHCOCH\overset{O}{-\!\!\!\diagdown\!\!\!\diagup\!\!\!-\!\!\!-}CHCONH_2 \qquad (4)$$

wherein $R_2$ is as defined for $R_2$ in the compound of formula (1) and wherein $R_3$, when $R_2$ is hydroxyl, is an amino acid or dipeptide residue corresponding to $R_1$ in the compound of formula (1) but with the or each free amino group therein in protected form, or $R_3$, when $R_2$ is an amino acid residue, is such that $R_3NH$ is a protected amino group.

Suitable amino protecting groups include alkoxycarbonyl groups, for example a tert-butoxycarbonyl group, which may be removed with an organic acid, for example trifluoroacetic acid, and also a benzyloxycarbonyl group which may be removed by treatment with a Lewis acid, for example boron tris(trifluoroacetate).

The compound (1) is obtained from the compound (4) through treatment with a reagent appropriate to effect removal of the protecting group $R_3$ or protecting group(s) present in $R_3$ in question. It may also be appropriate to treat the compound (1) with a suitable acid or base to effect salt formation and this may occur as a consequence of the removal of the protecting group so that, for example, the use of trifluoroacetic acid to remove an alkoxycarbonyl protecting group will form a trifluoroacetate. In such circumstances the compound can either be used in the salt form produced or the free compound can be generated by treatment with a base, for example an alkali metal hydroxide.

The compounds of formula (4) may conveniently be prepared and then deprotected as follows.

For the preparation of N-protected compounds of the formula (2) when $R_1$ is an amino acid residue, the mono-ethyl ester of D-trans-2,3-epoxysuccinic acid is activated and the activated acid is reacted with a salt of $N^2$-tert-butoxycarbonyl-L-2,3-diaminopropanoic acid in a polar organic solvent medium or in a mixture of such a solvent medium with water. The tert-butoxycarbonyl amino protecting group is removed from the resultant $N^2$-tert-butoxycarbonyl-$N^3$-D-trans-4-ethoxy-2,3-epoxysuccinyl-L-2,3-diaminopropanoic acid and the product is acylated with an active ester of the N-protected amino acid corresponding to the residue $R_1$, for example norvaline. After 4 to 10 hours the thus obtained analogue of the compound (4) in which the carbamoyl group is replaced by an ethoxy group is separated from the reaction mixture and the ester group is ammonolysed to gived the compound (4). The N-protecting group is then removed with trifluoroacetic acid to give the compound (2) in the form of a salt with trifluoroacetic acid which, where possible, is isolated by crystallisation.

For the preparation of N-protected compounds of the formula (2) when $R_1$ is a dipeptide residue, the corresponding compound in which $R_1$ is the C-terminal amino acid residue of the dipeptide residue is prepared in fully protected form, i.e. containing the N-protecting group(s) in the amino acid residue and also the 4-ethoxy group. The N-protecting group(s) is then removed with trifluoroacetic acid and the product is acylated with an active ester of the N-protected amino acid corresponding to the N-terminal amino acid residue of the dipeptide residue $R_1$. Ammonolysis, N-deprotection and salt formation are then effected as previously.

For the preparation of N-protected compounds of the formula (3) the mono-ethyl ester of D-trans-2,3-epoxysuccinic acid is activated and the activated acid is reacted with $N^2$-tert-butoxycarbonyl-L-2,3-diaminopropanoic acid in a polar organic solvent medium or in a mixture of such a solvent medium with water. The $N^2$-tert-butoxycarbonyl-$N^3$-D-trans-4-ethoxy-2,3-epoxysuccinyl-L-2,3-diaminopropanoic acid obtained is converted into an active ester which is then acylated by the amino acid corresponding to the residue $R_2$, for example norvaline. After 4 to 8 hours the thus obtained analogue of the compound (4) in which the carbamoyl group is replaced by an ethoxy group is separated from the reaction mixture. After ammonolysis of the ester group the amino group is deprotected with trifluoroacetic acid and the compound (3) is isolated in the form of a salt, where possible by crystallisation.

The activating agent used in such procedures is conveniently N-hydroxy-succinimide whilst the solvent medium is conveniently tetrahydrofuran, ethyl acetate or a mixture of an aliphatic alcohol such as methanol or ethanol with water. The procedures used are further illustrated by the specific examples which follow hereinafter.

Salts with an alternative acid than trifluoroacetic acid or, where appropriate, with a base are readily formed by reaction with the appropriate acid or base under suitable conditions.

The compounds (1) may be formulated with a physiologically acceptable diluent or carrier for use as pharmaceuticals for veterinary, for example in a mammalian context, and particularly for human use by a variety of methods. For instance, they may be applied as a composition incorporating a liquid diluent or carrier, for example an aqueous or oily solution, suspension or emulsion, which may be employed in injectable form for parenteral administration and therefore may conveniently be sterile and pyrogen free. Oral administration may also be used and compositions for this purpose may incorporate a liquid diluent or carrier, although it is more usual to use a solid, for example a conventional solid carrier material such as starch, lactose, dextrin or magnesium stearate. Such solid compositions may conveniently be of a formed type, for example as tablets, capsules (including spansules), etc.

Other forms of administration than by injection or through the oral route may also be considered in both human and veterinary contexts, for example the use of suppositories or pessaries. Another form of pharmaceutical composition is one for buccal or nasal administration, for example lozenges, nose drops or an aerosol spray. Of particular interest in the context of non-oral, non-parenteral administration are compositions for topical use in localised treatment of fungal or bacterial infections, such as creams, lotions and drops, as well as shampoos.

The compounds (1) of the present invention have been found to show a high level of antimicrobial activity, particularly antifungal activity, especially against *Candida albicans*. The antifungal activity of the compounds has been determined by the serial dilution method in a liquid YNB (Yeast Nitrogen Base) medium containing monosodium glutamate at a concentration of 200 µg/ml, with a temperature of 30° C. and an incubation time of 24 hours. It was found, for example, that the minimum inhibiting concentration (MIC) for the peptide $N^2$-L-norvalyl-$N^3$-trans-2,3-epoxysuccinamoyl-L-2,3-diaminopropanoic acid against *Candida albicans* ATCC 26278 is 0.15 µg/ml in the D-trans-2,3-epoxysuccinamoyl form and 0.25 µg/ml in the DL-trans-2,3-epoxysuccinamoyl form. By way of comparison the corresponding MIC for the peptide, $N^2$-L-alanyl-$N^3$-DLtrans-2,3-epoxysuccinamoyl-L-2,3-diaminopropanoic acid, i.e. the DL-trans form of Sch 3717, is 1.2 µg/ml.

The present invention thus includes the use of a compound of formula (1) as described hereinbefore for the manufacture of a medicament for use as an antimicrobial agent.

The levels of activity for the compounds (1) in the tests for antifungal activity indicated hereinbefore correspond to dosage levels for veterinary and human use in a range of about 1 to 50 mg/kg, particularly 3 to 20 mg/kg and especially 5 to 15 mg/kg, for example about 10 mg/kg. It will be appreciated, however, that in some circumstances it may be appropriate to use dose levels above or below these values. The doses appropriate for use against grain-positive or gram-negative bacteria are broadly similar but generally towards the higher end of these ranges. The compounds of the present invention have the advantage of high levels of antimicrobial activity, particularly antifungal activity, with quite low accompanying levels of toxicity. Without commitment to a specific mode of action it is believed that their activity is based on specific inhibition of the enzyme glucosamino-6-phosphate synthase which leads to the inhibition of cell-wall biosynthesis in the microbe.

The invention thus further includes a method for the treatment of fungal or bacterial diseases which comprises treating a patient in need thereof with a therapeutically effective amount of a compound of formula (1) as described hereinbefore.

The invention is illustrated by the following Examples. In these the identity of the derivatives obtained is confirmed by mass spectrometry, elemental analysis and proton magnetic resonance spectroscopy, the value of the mass ions being determined using the field desorption technique. The abbreviations of the compound names given in the titles of Examples 1 to 15 and used in the Table of Example 16 employ the usual three letter abbreviations for L-amino acid residues together with EADP for trans-2,3-epoxysuccinamoyl-L-2,3-diaminopropanoic acid. When the abbreviation EADP is used alone, the D form is indicated but when the compound is in the form of the diastereoisomeric mixture DL-EADP is used.

EXAMPLES

EXAMPLE 1

$N^2$-L-Norvalyl-$N^3$-D-trans-2,3-epoxysuccinamoyl-L-2,3-diaminopropanoic acid. (Nva-EADP)

(1) 4.08 g (20 mM of $N^2$-tert-butoxycarbonyl-L-2,3-diaminopropanoic acid are dissolved in a mixture of 50 ml water and 20 ml methanol and 1.68 g (20 mM) of sodium bicarbonate is added. The mixture is cooled to a temperature of 0° C. and 5.14 g (20 mM) of the N-succinimide ethyl ester of D-trans-2,3-epoxysuccinic acid are added, stirring vigorously. The reaction continues for 6 hours and then the methanol is evaporated off under reduced pressure and the residue acidified with a 10% solution of potassium bisulphate to a pH of 2. The product is extracted several times with ethyl acetate and the organic layer is washed with a saturated solution of sodium chloride and dried over anhydrous $MgSO_4$. The solvent is then evaporated off and the product is crystallised from an ethyl ether-hexane mixture to give 5.44 g (78%) of $N^2$-tert-butoxycarbonyl-$N^3$-D-trans-4-ethoxy-2,3 -epoxysuccinyl-L-2,3-diaminopropanoic acid, melting point 52°–54° C., $[\alpha]_{578}^{25}$=–54.2° (c=1, $CH_3OH$).

(2) 3.46 g (10 mM) of $N^2$-tert-butoxycarbonyl-$N^3$-D-trans-4-ethoxy-2,3epoxysuccinyl-L-2,3-diaminopropanoic acid are dissolved in 30 ml anhydrous trifluoroacetic acid, cooled to a temperature of 0° C. and left for 2 hours. The acid is then evaporated off, the residue flooded with dry ether and the sediment formed is dried in a vacuum desiccator to give 3.46 g (96%) of the trifluoroacetate of $N^3$-D-trans-4-ethoxy-2,3-epoxysuccinyl-L-2,3-diaminopropanoic acid, melting point 164°–166° C., $[\alpha]_{578}^{25}$=–71.2° (c=1, $CH_3OH$).

(3) To a cooled solution of 1.57 g (5 mM) of the N-hydroxysuccinimide ester of N-tert-butoxycarbonyl-L-norvaline in 20 ml of ethyl acetate, 0.7 ml of triethylamine and 1.85 g (5 mM) of the trifluoroacetate of $N^3$-D-trans-4-ethoxy-2,3-epoxysuccinyl-L-2,3-diaminopropanoic acid dissolved in 10 ml of methanol are added while stirring vigorously. The mixture is stirred for 8 hours and the solvent is then evaporated off. The residue is dissolved in 10 ml of water, a 10% solution of potassium bisulphate is added to give a pH of 2 and the product of the reaction is extracted several times with ethyl acetate. The organic layer is washed with a saturated solution of sodium chloride and dried over anhydrous $MgSO_4$. The solvent is then evaporated off to give 2.16 g (90%) of $N^2$-tert-butoxycarbonyl-L-norvalyl-$N^3$-D-trans4-ethoxy-2,3-epoxysuccinyl-L-2,3-diaminopropanoic acid, melting point 69°–70° C., $[\alpha]_{578}^{25}$=–14.2° (c=1, $CH_3OH$).

(4) 0.96 g (2 mM) of $N^2$-tert-butoxycarbonyl-L-norvalyl-$N^3$-D-trans4-ethoxy-2,3-epoxysuccinyl-L-2,3-diaminopropanoic acid are dissolved in 20 ml of a cold aqueous solution of ammonia (29%) and the solution is then stirred vigorously and left for 3 hours. The ammonia is evaporated off under reduced pressure at room temperature and the residue is dissolved in 20 ml water and poured onto a column of the ion exchanger material Amberlite CG 50 $H^+$. The column is washed with water, the effluent evaporated to dryness, and the residue is dried in a vacuum desiccator over solid KOH and then dissolved in 20 ml of cold trifluoroacetic acid and left for 3 hours. The trifluoroacetic acid is evaporated off under reduced pressure, ethyl ether is added to the residue and the sediment is dried in a vacuum desiccator to give 0.71 g (77%) of the trifluoroacetate of $N^2$-L-norvalyl-$N^3$-D-trans-2,3-epoxysuccinamoyl-L-2,3-diaminopropanoic acid, melting point 120°–122° C., $[\alpha]_{578}^{25}$=–20.2° (c=1, $CH_3OH$).

EXAMPLE 2

$N^2$-L-Norvalyl-$N^3$-DL-trans-2,3-epoxysuccinamoyl-L-2,3-diaminopropanoic acid (Nva-DL-EADP)

The procedure of Example 1 is followed but using DL-trans-2,3-epoxysuccinic acid in part (1) to give the trifluoroacetate of $N^2$-L-norvalyl-$N^3$-DL-trans-2,3-epoxysuccinamoyl-L-2,3-diaminopropanoic acid, $[\alpha]_{578}^{25}$=+9.8° (c=1, $CH_3OH$), as an amorphous solid in 75% yield in part (4).

EXAMPLES 3, 4, 5 AND 6

$N^2$-L-Leucyl-, $N^2$-L-methionyl-, $N^2$-L-2-aminobutanoyl- and $N^2$-L-valyl-$N^3$-D-trans-2,3-epoxysuccinamoyl-L-2,3-diaminopropanoic acid (Leu-EADP, Met-EADP, Abu-EADP and Val-EADP)

The procedure of Example 1 is followed but using the N-hydroxysuccinimide ester of N-tert-butoxycarbonyl-L-leucine, N-tert-butoxycarbonyl-L-methione, N-tert-butoxycarbonyl-L-2-aminobutanoic acid or N-tert-butoxycarbonyl-L-valine in part (3).

The following compounds are thus obtained in part (4) in the form of their trifluoroacetates which are amorphous solids without a defined melting point.

| Example | Compound | $[\alpha]_{578}^{25}$ (c = 1, CH$_3$OH) |
|---------|----------|------|
| 3 | $N^2$-L-leucyl-$N^3$-D-trans-2,3-epoxysuccinamoyl-L-2,3-diaminopropanoic acid | −12.8° |
| 4 | $N^2$-L-methionyl-$N^3$-D-trans-2,3-epoxysuccinamoyl-L-2,3-diaminopropanoic acid | −14.2° |
| 5 | $N^2$-L-2-aminobutanoyl-$N^3$-D-trans-2,3-epoxysuccinamoyl-L-2,3-diaminopropanoic acid | −18.4° |
| 6 | $N^2$-L-valyl-$N^3$-D-trans-2,3-epoxysuccinamoyl-L-2,3-diaminopropanoic acid | −10.4° |

EXAMPLE 7

$N^2$-L-Lysyl-L-norvalyl-$N^3$-D-trans-2,3-epoxysuccinamoyl-L-2,3-diaminopropanoic acid (Lys-Nva-EADP)

(1) 1.1 g (2.5 mM) of $N^2$-tert-butoxycarbonyl-L-norvalyl-$N^3$-D-trans-4-ethoxy-2,3-epoxysuccinyl-L-2,3-diaminopropanoic acid (prepared as described in Example 1) are dissolved in 10 ml of cold trifluoroacetic acid and left for 2 hours. The acid is then evaporated off under reduced pressure and dry ethyl ether is added to the residue. The sediment is filtered off and dried in a vacuum desiccator over KOH to give 0.93 g (90%) of the trifluoroacetate of $N^2$-L-norvalyl-$N^3$-D-trans-4-ethoxy-2,3-epoxysuccinamoyl-L-2,3-diaminopropanoic acid, melting point 102°–106° C., $[\alpha]_{578}^{25}$=−26.2° (c=1, CH$_3$OH).

(2) 0.88 g (2 mM) of the N-hydroxysuccinimide ester of $N^\alpha$,$N^\epsilon$-di-tert-butoxycarbonyl-L-lysine in 10 ml of tetrahydrofuran are added to a cooled solution of 0.94 g (2 mM) of the trifluoroacetate of $N^2$-L-norvalyl-$N^3$-D-trans4-ethoxy-2,3-epoxysuccinamoyl-L-2,3-diaminopropanoic acid in 10 ml methanol and 0.2 ml triethylamine and the mixture stirred vigorously. Stirring is continued for 8 hours, after which the solvents are evaporated off. The residue is dissolved in 10 ml of water, a 10% solution of potassium bisulphate is added to give a pH of 2 and the product of the reaction is extracted several times with ethyl acetate. The organic layer is washed with a saturated solution of sodium chloride and dried over anhydrous MgSO$_4$. The solvent is then evaporated off to give 1.07 g (82%) of $N^2$-$N^\alpha$,$N^\epsilon$-(bis-tert-butoxycarbonyl-L-lysyl)-L-norvalyl)-$N^3$-D-trans-4-ethoxy-2,3-epoxysuccinamoyl-L-2,3-diaminopropanoic acid, melting point 79°–81° C., $[\alpha]_{578}^{25}$=−47.2° (c=1, CH$_3$OH).

(3) 0.98 g (1.5 mM) of $N^2$-$N^\alpha$,$N^\epsilon$-(bis-tert-butoxycarbonyl-L-lysyl)-L-norvalyl)-$N^3$-D-trans-4-ethoxy-2,3-epoxysuccinamoyl-L-2,3-diaminopropanoic acid are dissolved in 20 ml of a cold aqueous solution of ammonia (28%) and left for 3 hours. The ammonia is evaporated off under reduced pressure at room temperature and the residue is dissolved in 5 ml of water and poured onto a column of the ion exchange material Amberlite CG 50 H$^+$. The column is washed with water, the effluent is concentrated until dry and the residue is dried over KOH in a vacuum desiccator and then dissolved in 20 ml of cold trifluoroacetic acid and left for 3 hours. The acid is evaporated off under reduced pressure and dry ethyl ether is added to the residue. The sediment is washed with ether and dried over KOH in a vacuum desiccator to give 0.75 g (68%) of the di-trifluoroacetate of $N^2$-L-lysyl-L-norvalyl-$N^3$-D-trans-2,3-epoxysuccinamoyl-L-2,3-diaminopropanoic acid as an amorphous solid, $[\alpha]_{578}^{25}$=−9.8° (c=1, CH$_3$OH).

EXAMPLE 8

$N^2$-L-Lysyl-L-norvalyl-$N^3$-DL-trans-2,3-epoxysuccinamoyl-L-2,3-diaminopropanoic acid (Lys-Nva-DL-EADP)

The procedure of Example 7 is followed but using $N^2$-tert-butoxycarbonyl-L-norvalyl-$N^3$-DL-trans-4-ethoxy-2,3-epoxysuccinyl-L-2,3-diaminopropanoic acid (prepared as described in Example 2) in part (1) to give the trifluoroacetate of $N^2$-L-lysyl-L-norvalyl-$N^3$-DL-trans-2,3-epoxysuccinamoyl-L-2,3-diaminopropanoic acid $[\alpha]_{578}^{25}$= −4.8° (c=1, CH$_3$OH) as an amorphous solid in 66% yield in part (3).

EXAMPLES 9, 10 AND 11

$N^2$-L-Norvalyl-L-norvalyl-, $N^2$-L-glutamyl-L-norvalyl- and $N^2$-L-methionyl-L-norvalyl-$N^3$-D-trans-2,3-epoxysuccinamoyl-L-2,3-diaminopropanoic acid The procedure of Example 7 is followed but using the N-hydroxysuccinimide ester of N-tert-butoxycarbonyl-L-norvaline, N-tert-butoxycarbonyl-L-glutamine or N-tert-butoxycarbonyl-L-methionine in part (2).

The following compounds are thus obtained in part (3) in the form of their trifluoroacetates which are amorphous solids without a defined melting point.

| Example | Compound | $[\alpha]_{578}^{25}$ (c = 1, CH$_3$OH) |
|---------|----------|------|
| 9 | $N^2$-L-norvalyl-L-norvalyl-$N^3$-D-trans-2,3-epoxysuccinamoyl-L-2,3-diaminopropanoic acid | −4.8° |
| 10 | $N^2$-L-glutamyl-norvalyl-$N^3$-D-trans-2,3-epoxysuccinamoyl-L-2,3-diaminopropanoic acid | −7.2° |
| 11 | $N^2$-L-methionyl-L-norvalyl-$N^3$-D-trans-2,3-epoxysuccinamoyl-L-2,3-diaminopropanoic acid | −3.3° |

EXAMPLE 12

$N^3$-D-trans-2,3-Epoxysuccinamoyl-L-2,3-diaminopropionyl-L-norvaline (EADP-Nva)

(1) 1.04 g (3 mM) of $N^2$-tert-butoxycarbonyl-$N^3$-D-trans-4-ethoxy-2,3-epoxysuccinyl-L-2,3-diaminopropanoic acid [prepared as described for the DL-trans compound by Andruszkiewicz in J. Antibiotics, 1994, 47, 380 but starting from mono-ethyl D-trans-2,3-epoxysuccinate which is itself prepared according to the method described in Chem. Pharm. Bull., 1987, 35, 1098] and 0.35 g (3 mM) of N-hydroxysuccinimide are dissolved in 20 ml of ethyl acetate and cooled to 0° C. 0.68 g (3.3 mM) of dicyclohexylcarbodimide in 10 ml ethyl acetate are then added and the reaction is allowed to proceed for 1 hour at 0° C. and then for 24 hours at room temperature. The dicyclohexyl urea produced is filtered off, the filtrate is evaporated to dryness under reduced pressure and the residue is crystallised from an ethyl ether-hexane mixture to give 1.22 g (92%) of the N-hydroxysuccinimide ester of $N^2$-tert-butoxycarbonyl-$N^3$-D-trans-4-ethoxy-2,3-epoxysuccinyl-L-2,3-diaminopropanoic acid, melting point 120°–122° C., $[\alpha]_{578}^{25}$=−70.2° (c=1, CH$_3$OH).

(2) 0.89 g (2 mM) of the N-hydroxysuccinimide ester of N$^2$-tert-butoxycarbonyl-N$^3$-D-trans-4-ethoxy-2,3-epoxysuccinyl-L-2,3-diaminopropanoic acid dissolved in 5 ml methanol are added to a cooled solution of 0.23 g (2 mM) of L-norvaline and 0.17 g (2 mM) of sodium bicarbonate in 10 ml of water and 10 ml of methanol with vigorous stirring. The mixture is left for 12 hours and the solvent is then evaporated off, the residue is dissolved in 10 ml of water and acidified with a 10% solution of potassium bicarbonate to a pH of 2, and the product of the reaction is extracted with ethyl acetate. The organic layer is washed with water, dried over anhydrous MgSO$_4$ and evaporated to give 1.46 g (71%) of N$^2$-tert-butoxycarbonyl-N$^3$ -D-trans-4-ethoxy-L-2,3-epoxysuccinyl-L-2,3-diaminopropionyl-L-valine, $[\alpha]_{578}^{25}$=−25.4° (c=1, CH$_3$ OH).

(3) 0.48 g (1 mM) of N$^2$-tert-butoxycarbonyl-N$^3$-D-trans-4-ethoxy-L-2,3-epoxysuccinyl-L-2,3-diaminopropionyl-L-norvaline are dissolved in 15 ml of a cold aqueous solution of ammonia (29%) and left for 3 hours. The ammonia is evaporated off under reduced pressure at room temperature. The residue is dissolved in 5 ml water and poured onto a column of the ion exchange material Amberlite CG 50 H$^+$. The column is washed with water, the effluent is concentrated until dry and the residue is dried over KOH in a vacuum desiccator, then treated with cold trifluoroacetic acid (10 ml) and left for 3 hours. The acid is evaporated off under reduced pressure and the residue is treated with dry ether. The sediment is dried over KOH in a vacuum desiccator to give 0.3 g (70%) of N$^3$-D-trans-2,3-epoxysuccinamoyl-L-2,3-diaminopropionyl-L-norvaline trifluoroacetate (EADP-Nva), $[\alpha]_{578}^{25}$=−21.2° (c=1, CH$_3$OH) as an amorphous solid.

EXAMPLE 13

N$^3$-DL-trans-2,3-Epoxysuccinamoyl-L-2,3-diaminopropionyl-L-norvaline (DL-EADP-Nva)

The procedure of Example 12 is followed but using N$^2$-tert-butoxycarbonyl-N$^3$-DL-trans-4-ethoxy-2,3-epoxysuccinyl-L-2,3-diaminopropanoic acid [prepared as described by Andruskiewicz, J. Antibiotics, 1994, 47, 380] in part (1) to give the trifluoroacetate of N$^3$-DL-trans-2,3-epoxysuccinamoyl-L-2,3-diaminopropionyl-L-norvaline, $[\alpha]_{578}^{25}$=−8.0° (c=1, CH$_3$OH) as an amorphous solid with a 70% yield in part (3).

EXAMPLES 14 AND 15

N$^3$-D-trans-2,3-Epoxysuccinamoyl-L-2,3-diaminopropionyl-L-methionine (EADP-Met) and N$^3$-D-trans-2,3-epoxysuccinamoyl-L-2,3-diaminopropionyl-L-2-aminobutanoic acid (EADP-Abu)

The procedure of Example 12 is followed but using L-methionine or L-2-aminobutanoic acid in part (2).

The following compounds are thus obtained in part (3) in the form of their trifluoroacetates which are amorphous solids without a defined melting point.

| Example | Compound | $[\alpha]_{578}^{25}$ (c = 1, CH$_3$OH) |
|---|---|---|
| 14 | N$^3$-D-trans-2,3-epoxysuccinamoyl-L-2,3-diaminopropionyl-L-methionine | −15.4° |
| 15 | N$^3$-D-trans-2,3-epoxysuccinamoyl-L-2,3-diaminopropionyl-L-2-aminobutanoic acid | −19.8° |

EXAMPLE 16

Antifungal Activity

The minimum inhibiting concentrations (MIC) in mg/ml were determined for the compounds of Examples 1, 2, 7, 8, 12 and 13 against various *Candida sp.* using the broth serial dilution method of Milewski et al., Drugs Exp. Clin. Res., 1988, 14, 461. A liquid Yeast Nitrogen Base (YNB)-Difco medium containing 200 µg/ml sodium glutamate was used with a content of 10$^5$ cells/ml at a temperature of 30° C. and with an incubation time of 24 hours.

By way of comparison, the diastereoisomeric mixture corresponding to Sch 3717, N$^2$-L-alanyl-N$^3$-DL-trans-2,3-epoxysuccinamoyl-L-2,3-diaminopropanoic acid was also tested under similar conditions.

The results are shown in the following Table from which it will be seen that the compounds containing an EDAP group in the DL form are generally less active than those in which the group is of the L form. All compounds are more active than Ala-DL-EADP.

| Compound | C. albicans ATTC 26278 | C. albicans 2043 | C. krusei | C. glabrata | C. famata 1940 |
|---|---|---|---|---|---|
| Ala—DL—EADP$^{(1)}$ | 1.2 | 1.0 | — | 1.5 | — |
| Nva—EADP | 0.15 | 0.1 | 0.35 | 0.5 | 0.35 |
| Nva—DL—EADP | 0.25 | 0.25 | 0.35 | 0.75 | 0.5 |
| Lys—Nva—EADP | 0.2 | 0.25 | 0.75 | 0.5 | 0.5 |
| Lys—Nva—DL—EADP | 0.5 | 0.5 | 1.5 | 0.75 | 1.0 |
| EADP—Nva | 0.4 | 0.5 | 0.8 | 1.0 | 0.5 |
| DL—EADP—Nva | 0.5 | 0.75 | 1.0 | 1.25 | 0.75 |

$^{(1)}$A dash under a particular Candida sp. indicates the compound was not tested against that fungal strain.

We claim:

1. A compound being a derivative of $N^3$-D-trans-2,3-epoxysuccinamoyl-L-2,3-diaminopropanoic acid of formula (I)

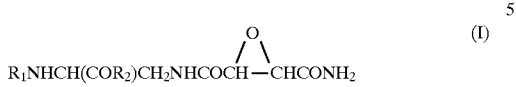

wherein $R_1$ is hydrogen;

or $R_1$ is the residue of an amino acid selected from L-valine, L-leucine, L-isoleucine, L-norleucine, L-methionine, L-lysine, L-2-aminobutanoic acid, L-aspartic acid and L-glutamic acid;

or $R_1$ is the residue of a dipeptide selected from L-norvalyl-L-norvaline, L-lysyl-L-norvaline, L-methionyl-L-norvaline, L-glutamyl-L-norvaline, L-norvalyl-L-methionine, L-methionyl-L-methionine, L-leucyl-L-norvaline, L-norleucyl-L-norvaline, L-valyl-L-norvaline, L-glutamyl-L-leucine, L-asparginyl-L-norvaline and L-leucyl-L-leucine:

wherein $R_2$ is hydroxyl;

or $R_2$ is the residue of an amino acid selected from L-alanine, L-methionine, L-norvaline, L-leucine, L-norleucine and L-2-aminobutanoic acid; with the provisos that when $R_1$ is hydrogen then $R_2$ is an amino acid residue and that when $R_1$ is an amino acid residue or a peptide residue then $R_2$ is hydroxyl; the compound optionally being in the form of a physiologically acceptable salt.

2. A compound according to claim 1 of formula (2)

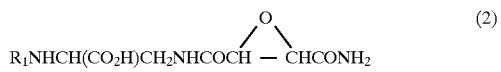

wherein $R_1$ is the residue of an amino acid or the residue of a dipeptide as defined in claim 1.

3. A compound according to claim 2, wherein $R_1$ is the residue of an amino acid.

4. A compound according to claim 3, wherein the amino acid is L-methionine or L-leucine.

5. A compound according to claim 1 of formula (3)

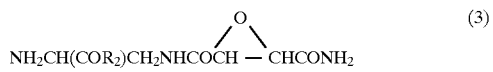

wherein $R_2$ is the residue of an amino acid as defined in claim 1.

6. A compound according to claim 1 being $N^2$-L-lysyl-L-norvalyl-$N^3$D-trans-2,3-epoxysuccinamoyl-L-2,3-diaminopropanoic acid.

7. A compound according to claim I being $N^3$-D-trans-2,3-epoxysuccinamoyl-L-2,3-diaminopropionyl-L-norvaline.

8. A compound according to any of claim 1 in the form of the salt with trifluoroacetic acid.

9. A process for the preparation of a compound of formula (1) according to claim 1 which comprises treating a compound of formula (4)

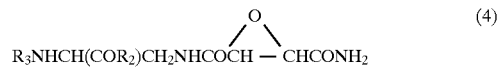

wherein $R_2$ is as defined for $R_2$ in the compound of formula (1); and wherein $R_3$, when $R_2$ is hydroxyl, is an amino acid or dipeptide residue corresponding to $R_1$ in the compound of formula (1) but with the or each free amino group in protected form;

or $R_3$, when $R_2$ is an amino acid residue, is a protected amino group; to remove the protecting group(s) in $R_3$, and, where appropriate, converting the compound of formula (1) to a physiologically acceptable salt thereof.

10. A process according to claim 9, wherein the protecting group is a tert-butoxycarbonyl group.

11. A pharmaceutical composition comprising a compound of formula (1) according to claim 1 together with a physiologically acceptable diluent or carrier.

12. A method for the treatment of fungal or bacterial diseases which comprises treating a patient in need thereof with a therapeutically effective amount of a compound of formula (1) according to claim 1.

13. A method according to claim 12, wherein the patient has a *Candida albicans* infection.

14. A method for the treatment of fungal or bacterial diseases which comprises administering a therapeutically effective amount of a compound of formula (I) according to claim 1, wherein the compound is administered parenterally, through oral, nasal or buccal route or through suppository or pessary.

15. A method according to claim 14 wherein the compound is administered parenterally or orally.

16. A method for the treatment of fungal or bacterial diseases which comprises treating a patient in need thereof with a therapeutically effective amount of a compound of formula (1)

wherein $R_1$ is hydrogen;

or $R_1$ is the residue of an amino acid selected from L-valine, L-norvaline, L-leucine, L-isoleucine, L-norleucine, L-methionine, L-lysine, L-2-aminobutanoic acid, L-aspartic acid and L-glutamic acid;

or $R_1$ is the residue of a dipeptide selected from L-norvalyl-L-norvaline, L-lysyl-L-norvaline, L-methionyl-L-norvaline, L-glutamyl-L-norvaline, L-norvalyl-L-methionine, L-methionyl-L-methionine, L-leucyl-L-norvaline, L-norleucyl-L-norvaline, L-valyl-L-norvaline, L-glutamyl-L-leucine, L-asparginyl-L-novaline and L-leucyl-L-leucine;

wherein $R_2$ is hydroxyl;

or $R_2$ is the residue of an amino acid selected from L-alanine, L-methionine, L-valine, L-norvaline, L-leucine, L-isoleucine, L-norleucine and L-2-aminobutanoic acid; with the proviso that when $R_1$ is hydrogen then $R_2$ is an amino acid residue and that when $R_1$ is an amino acid residue or a peptide residue then $R_2$ is hydroxyl;

the compound optionally being in the form of a physiologically acceptable salt.

17. A method according to claim 16, wherein the patient has a *Candida albicans* infection.

18. A method for the treatment of fungal or bacterial diseases which comprises administering a therapeutically effective amount of a compound of formula (1)

wherein $R_1$ is the residue of an amino acid selected from L-valine, L-norvaline, L-leucine, L-isoleucine, L-norleucine, L-methionine, L-lysine, L-2-aminobutanoic acid, L-aspartic acid and L-glutamic acid;

or $R_1$ is the residue of a dipeptide selected from L-norvalyl-L-norvaline, L-lysyl-L-norvaline, L-methionyl-L-norvaline, L-glutamyl-L-norvaline, L-norvalyl-L-methionine, L-methionyl-L-methionine, L-leucyl-L-norvaline, L-norleucyl-L-norvaline, L-valyl-L-norvaline, L-glutamyl-L-leucine, L-asparginyl-L-norvaline, and L-leucyl-L-leucine; wherein $R_2$ is hydroxyl;

or $R_2$ is the residue of an amino acid selected from L-alanine, L-methionine, L-valine, L-norvaline, L-leucine, L-isoleucine, L-norleucine and L-2-aminobutanoic acid;

with the provisos that when $R_1$ is hydrogen then $R_2$ is an amino acid residue and that when $R_1$ is an amino acid residue or a peptide residue then $R_2$ is an amino acid residue and that when $R_1$ is an amino acid residue or a peptide residue then R is hydroxyl;

the compound optionally being in the form of a physiologically acceptable salt;

wherein the compound is administered parentally; through oral, nasal or buccal route; or through suppository or pessary.

19. A method according to claim 18, wherein the compound is administered parenterally or orally.

20. A method according to claim 18, wherein $R_1$ is L-norvalyl or L-lysyl-L-norvalyl.

* * * * *